US008718344B2

(12) United States Patent
Kobayashi et al.

(10) Patent No.: US 8,718,344 B2
(45) Date of Patent: May 6, 2014

(54) IMAGE PROCESSING APPARATUS AND MEDICAL IMAGE DIAGNOSIS APPARATUS

(75) Inventors: Tadaharu Kobayashi, Otawara (JP); Takayuki Ishikawa, Nasushiobara (JP); Shingo Abe, Nasushiobara (JP)

(73) Assignees: Kabushiki Kaisha Toshiba, Tokyo (JP); Toshiba Medical Systems Corporation, Otawara-Shi (JP)

(*) Notice: Subject to any disclaimer, the term of this patent is extended or adjusted under 35 U.S.C. 154(b) by 157 days.

(21) Appl. No.: 13/153,921

(22) Filed: Jun. 6, 2011

(65) Prior Publication Data
US 2011/0299746 A1 Dec. 8, 2011

(30) Foreign Application Priority Data

Jun. 7, 2010 (JP) ................................. 2010-130270
Apr. 28, 2011 (JP) ................................. 2011-101501

(51) Int. Cl.
*G06K 9/00* (2006.01)
(52) U.S. Cl.
USPC ........................................................ 382/131
(58) Field of Classification Search
USPC .................... 382/128–134; 128/920–925; 356/39–49; 600/407–414, 424–426; 345/581–618
See application file for complete search history.

(56) References Cited

U.S. PATENT DOCUMENTS

| 2001/0031920 A1* | 10/2001 | Kaufman et al. ............. 600/431 |
| 2004/0015070 A1* | 1/2004 | Liang et al. .................. 600/407 |
| 2005/0043614 A1* | 2/2005 | Huizenga et al. ............. 600/427 |
| 2006/0193510 A1* | 8/2006 | Matsumoto ................... 382/154 |

FOREIGN PATENT DOCUMENTS

| CN | 1929781 A | 3/2007 |
| JP | 11-76228 A | 3/1999 |

OTHER PUBLICATIONS

Chinese Office Action with its English translation for Chinese Patent Application No.: 201110158654.3 mailed on Feb. 7, 2014.

* cited by examiner

*Primary Examiner* — Atiba O Fitzpatrick
(74) *Attorney, Agent, or Firm* — Yoshida & Associates, LLC

(57) ABSTRACT

An image processing apparatus and a medical image diagnosis apparatus comprise a creation unit, a designation unit, a measurement unit, and a display control unit. The creation unit is configured to create a virtual endoscopic image observed using a preset viewpoint position and a preset line-of-sight direction based on 3-dimensional image data. The designation unit is configured to analyze the 3-dimensional image data to designate a plaque portion and/or a calcification portion. The measurement unit is configured to measure information on spatial distribution of the plaque portion and/or the calcification portion designated by the designation unit. The display control unit is configured to perform control to display the virtual endoscopic image created by the creation unit and the information on spatial distribution measured by the measurement unit.

12 Claims, 15 Drawing Sheets

FIG.3

| THICKNESS OF PLAQUE/LIME (VOXEL NUMBER) | COLOR SETTING |
|---|---|
| 1 TO 10 | BLUE COLOR DENSITY 1 |
| 11 TO 20 | BLUE COLOR DENSITY 2 |
| 21 TO 30 | BLUE COLOR DENSITY 3 |
| ⋮ | ⋮ |

(A)

(B)

IMAGE PROCESSING APPARATUS AND MEDICAL IMAGE DIAGNOSIS APPARATUS

CROSS-REFERENCE TO RELATED APPLICATIONS

This application is based upon and claims the benefit of priority from Japanese Patent Application No. 2010-130270, filed on Jun. 7, 2010; and Japanese Patent Application No. 2011-101501, filed on Apr. 28, 2011, the entire contents of all of which are incorporated herein by reference.

FIELD

Embodiments described herein relate generally to an image processing apparatus and a medical image diagnosis apparatus.

BACKGROUND

In the related art, there is known a method of creating a virtual endoscopic image based on 3-dimensional image data collected by a medical image diagnosis apparatus (hereinafter, referred to as a virtual endoscope (VE) method). Examples of the medical image diagnosis apparatus include an X-ray computed tomography (CT) apparatus, a magnetic resonance imaging (MRI) apparatus, an ultrasonograph apparatus, and the like. In the VE method, the image processing apparatus receives settings for a viewpoint position, a line-of-sight direction, and a field-of-view angle that centers on the line-of-sight direction. In addition, the image processing apparatus creates a projection image by perspectively projecting the 3-dimensional image data at a viewpoint position onto the range defined by a line-of-sight direction and a field-of-view angle.

Since the projection image created using the VE method is similar to an endoscope image obtained by observing a surface (internal surface) inside an organ using an endoscope, it is called a virtual endoscopic image (hereinafter, referred to as a fly-through image). For example, since a fly-through image created from the 3-dimensional image data obtained by capturing a vessel of a subject is similar to an endoscopic image obtained by observing a surface (a vascular wall) inside the vessel, it is used in an ischemic heart disease diagnosis. For example, JP-A 11-76228 (KOKAI) discloses a technique of synthesizing a cross-sectional image created from the 3-dimensional image data with a fly-through image.

However, the image processing apparatus of the related art only displays information on the surface of the projection image as described above, and fails to display, for example, information on spatial distribution such as a thickness of a plaque portion or a calcification portion formed in the vascular wall. For example, although the spatial distribution information on the plaque portion or the calcification portion is important in an ischemic heart disease diagnosis, the image processing apparatus of the related art cannot provide such information.

BRIEF DESCRIPTION OF THE DRAWINGS

FIG. 3 is a diagram illustrating a matching table between a voxel number and color setting.

DETAILED DESCRIPTION

The image processing apparatus according to the present embodiments includes a creation unit, a designation unit, a measurement unit, and a display control unit. The creation unit is configured to create a virtual endoscopic image observed using a preset viewpoint position and a preset line-of-sight direction based on 3-dimensional image data collected by a medical image diagnosis apparatus. The designation unit is configured to analyze the 3-dimensional image data and designates a plaque portion and/or a calcification portion. The measurement unit is configured to measure information on spatial distribution of the plaque portion and/or the calcification portion designated by the designation unit. The display control unit is configured to perform control such that the virtual endoscopic image created by the creation unit and information on the spatial distribution measured by the measurement unit are displayed.

Figure 1:
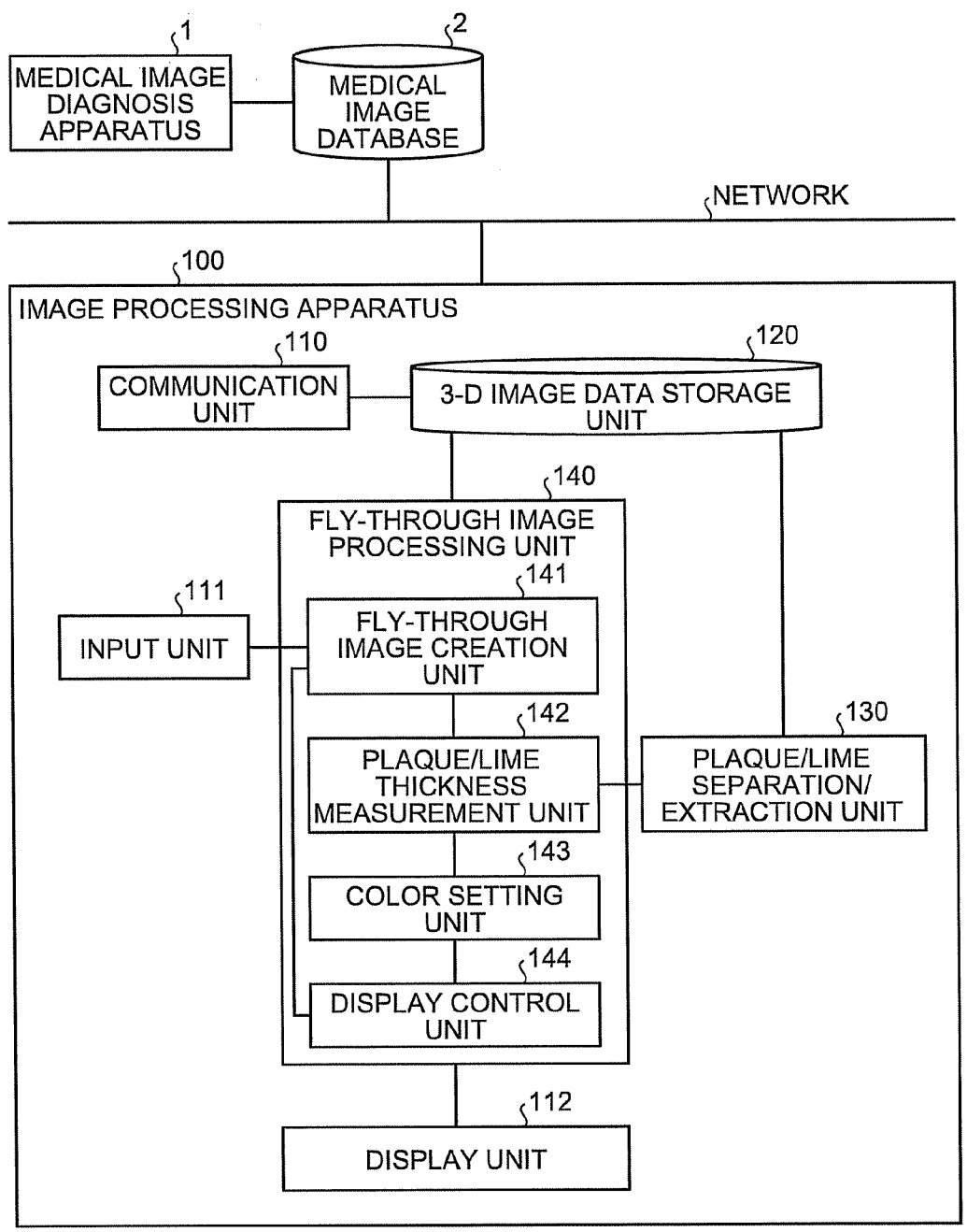
FIG. 1 is a block diagram illustrating the configuration of an image processing apparatus according to a first embodiment.

First, the configuration of an image processing apparatus 100 according to a first embodiment will be described. FIG. 1 is a block diagram illustrating the configuration of the image processing apparatus 100 according to the first embodiment. Referring to FIG. 1, the image processing apparatus 100 according to the first embodiment is connected with a medical image database 2 via a network. In addition, the medical image database 2 is connected with a medical image diagnosis apparatus 1.

Although description of the first embodiment will be made about a configuration example in which the image processing apparatus 100 is connected with the medical image diagnosis apparatus 1 and the medical image database 2 via a network, and the medical image database 2 and the medical image diagnosis apparatus 1 are contained in separate casings, but this is just an example and is not intended to limit the embodiment. For example, the image processing apparatus 100 may be assembled in the internal side of the medical image diagnosis apparatus 1. Alternatively, the medical image database 2 may be assembled in the internal side of the medical image diagnosis apparatus 1. Although the medical image database 2 is connected with a single medical image diagnosis apparatus 1 in FIG. 1, it may be connected with a plurality of medical image diagnosis apparatuses 1 such as X-ray CT, MRI, and ultrasonograph apparatuses.

The medical image diagnosis apparatus 1 according to the first embodiment collects 3-dimensional image data. Examples of the medical image diagnosis apparatus 1 include an X-ray CT apparatus that collects 3-dimensional X-ray CT images, an MRI apparatus that collects 3-dimensional MRI images, an ultrasonograph apparatus that collects 3-dimensional ultrasonic images, and the like. The medical image database 2 according to the first embodiment stores 3-dimensional image data collected by the medical image diagnosis apparatus 1. For example, the medical image database 2 may be a picture archiving and communication system (PACS) for managing medical images, an electronic medical chart system database for managing medical images attached electronic medical charts, and the like.

Here, the image processing apparatus 100 according to the first embodiment obtains 3-dimensional image data designated by an operator such, such as a doctor from the medical image database 2, performs image processing on the obtained 3-dimensional image data, and then, delivers the results to the operator. Specifically, the image processing apparatus 100 according to the first embodiment creates a fly-through image from the 3-dimensional image data through the image processing, analyzes the 3-dimensional image data, and designates a plaque portion or a calcification portion. In addition, the image processing apparatus 100 measures the thickness of the plaque or calcification portion and displays the information of the thickness as well as the fly-through image. Hereinafter, the image processing performed by the image processing apparatus 100 according to the first embodiment will be described with reference to FIGS. 1, 2A, 2B, 3, 4A to 4F, 5A to 5F, 6A, and 6B.

As shown in FIG. 1, the image processing apparatus 100 according to the first embodiment includes a communication unit 110, an input unit 111, a display unit 112, a 3-dimensional image data storage unit 120, a plaque/lime separation/extraction unit 130, and a fly-through image processing unit 140.

The communication unit 110 performs communication with the medical image database 2 to obtain 3-dimensional image data from the medical image database 2. The input unit 111 receives instructions or the like for manipulating the image processing apparatus 100 from the operator. Examples of the input unit 111 include a mouse, a keyboard, a microphone, or the like. The display unit 112 displays a graphical user interface (GUI) for receiving instructions or the like for manipulating the image processing apparatus 100, a fly-through image, and the like. For example, the display unit 112 is a display monitor or the like.

The 3-dimensional image data storage unit 120 stores the 3-dimensional image data obtained from the medical image database 2 using the communication unit 110. The 3-dimensional image data storage unit 120 is, for example, a semiconductor memory device, such as a random access memory (RAM) or a flash memory, a hard disk, or an optical disk. The following description is given for an exemplary case in which 3-dimensional X-RAY CT images obtained by image-capturing a blood vessel of a subject P are acquired from the medical image database 2 through the operator's designation. In addition, the embodiment may be similarly applied to a case where 3-dimensional MRI images or 3-dimensional ultrasonic images obtained by image-capturing a blood vessel of the subject P and the like are acquired. In addition, the embodiment may be similarly applied to a case where portions other than the blood vessel are subjects to be image-captured.

The plaque/lime separation/extraction unit 130 analyzes the 3-dimensional image data and designates a vascular wall, a plaque portion, and a calcification portion. Specifically, the plaque/lime separation/extraction unit 130 analyzes the 3-dimensional image data read from the 3-dimensional image data storage unit 120 and separates/extracts the vascular wall, the plaque portion, and the calcification portion, for example, through threshold processing of the CT values or the like. For example, The plaque/lime separation/extraction unit 130 is implemented by an integrated circuit, such as an application specific integrated circuit (ASIC) or a field programmable gate array (FPGA), or an electronic circuit, such as a central processing unit (CPU) or a micro processing unit (MPU).

That is, the plaque/lime separation/extraction unit 130 analyzes the CT values of each pixel contained in the 3-dimensional image data and separates/extracts pixels of which the CT values are within the range of a threshold value representing the vascular wall, as the vascular wall. In addition, the plaque/lime separation/extraction unit 130 analyzes the CT values of each pixel contained in the 3-dimensional image data and separates/extracts pixels of which the CT values are within the range of a threshold value representing the plaque portion, as the plaque portion. In addition, the plaque/lime separation/extraction unit 130 analyzes the CT values of each pixel contained in the 3-dimensional image data and separates/extracts pixels of which the CT values are in the range of a threshold value representing the calcification portion, as the calcification portion. In addition, the plaque/lime separation/extraction unit 130 sends information on the pixels separated/extracted as the plaque portion and the calcification portion to the plaque/lime thickness measurement unit 142. In addition, the separation/extraction may be implemented by applying a threshold value method known in the art.

As shown in FIG. 1, the fly-through image processing unit 140 includes a fly-through image creation unit 141, a plaque/lime thickness measurement unit 142, a color setting unit 143, and a display control unit 144. For example, the fly-through image processing unit 140 is implemented by an integrated circuit, such as an application specific integrated circuit (ASIC) or a field programmable gate array (FPGA), or an electronic circuit, such as a central processing unit (CPU) or a micro processing unit (MPU).

The fly-through image creation unit 141 creates the fly-through image from the 3-dimensional image data. Specifically, first, the fly-through image creation unit 141 receives settings for parameters including a viewpoint position, a line-of-sight direction, and a field-of-view angle from an operator through the input unit 111. Next, the fly-through image creation unit 141 creates the fly-through image by perspectively projecting the 3-dimensional image data read from the 3-dimensional image data storage unit 120 in a radial fashion onto a range defined by the line-of-sight direction and the field-of-view angle from the viewpoint position. In addition, the fly-through image creation unit 141 notifies the plaque/lime thickness measurement unit 142 of parameters including the viewpoint position, the line-of-sight direction, and the field-of-view angle and sends the created fly-through image to the display control unit 144.

The plaque/lime thickness measurement unit 142 measures information on spatial distribution of the plaque portion and the calcification portion based on a preset viewpoint position. Specifically, first, the plaque/lime thickness measurement unit 142 receives notification of parameters including the viewpoint position, the line-of-sight direction, and the field-of-view angle from the fly-through image creation unit 141. Next, the plaque/lime thickness measurement unit 142 measures the thicknesses of the plaque portion and the calcification portion using the separation/extraction information on the plaque and lime portions sent from the plaque/lime separation/extraction unit 130 and the parameters including the viewpoint position, the line-of-sight direction, and the field-of-view angle notified from the fly-through image creation unit 141. In addition, the plaque/lime thickness measurement unit 142 notifies the color setting unit 143 of the measured thickness information.

Figure 2A:
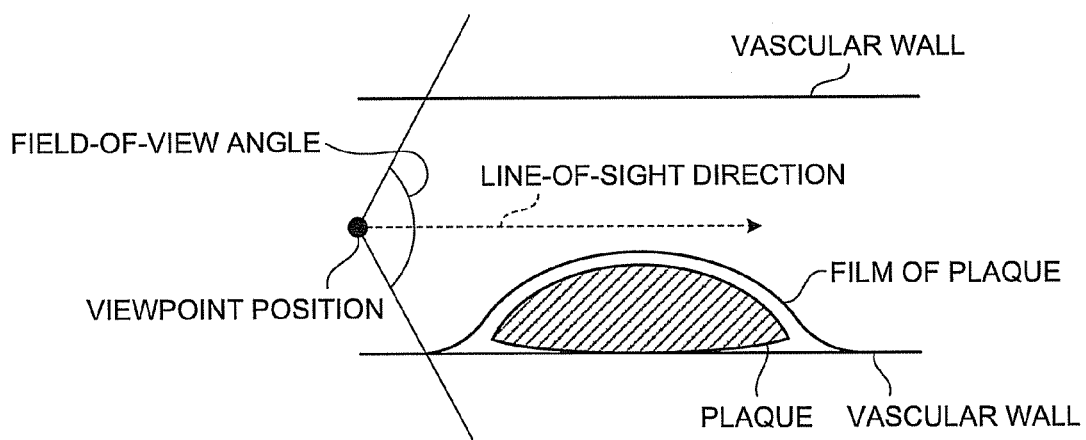
FIG. 2A is a diagram illustrating measurement of thicknesses of a plaque portion and a calcification portion according to the first embodiment.
Figure 2B:
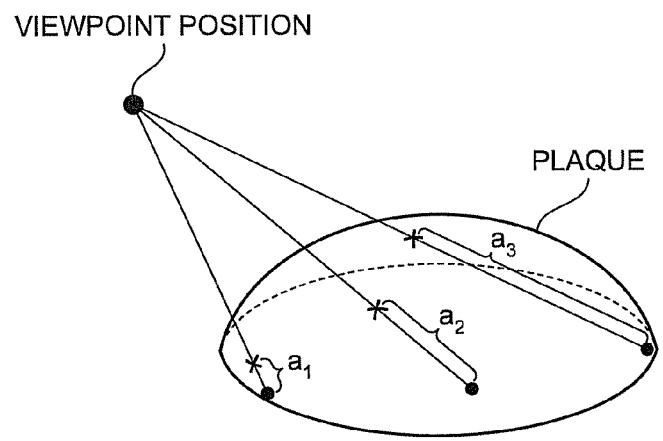
FIG. 2B is a diagram illustrating measurement of thicknesses of a plaque portion and a calcification portion according to the first embodiment.

FIGS. 2A and 2B are diagrams illustrating measurement of the thickness of the plaque portion and the calcification portion. FIG. 2A shows a relationship between information including the viewpoint position, the line-of-sight direction, and the field-of-view angle and the plaque portion formed in a vascular wall. As shown in FIG. 2A, it is assumed that, for example, the plaque portion adheres to the vessel as if it bulges.

FIG. 2B illustrates measurement of the thickness of the plaque portion using a preset viewpoint position and a preset line-of-sight direction. As shown in FIG. 2B, it is assumed that, for example, the plaque portion has a partly-cut-out spherical shape. The shape of the plaque portion illustrated in FIG. 2B is not more than an example given for the purpose of simplicity in description, and the embodiment may be similarly applied to a case where the plaque portion has any other shape.

In this case, for example, the plaque/lime thickness measurement unit 142 performs search in a radial fashion toward the entire plaque portion by using the viewpoint position as a starting point (origin point). In addition, the plaque/lime thickness measurement unit 142 counts up the number of pixels (voxel number) having the CT value representing a "plaque" along each straight line drawn from the viewpoint position to the plaque portion. For example, reference numerals $a_1$, $a_2$, and $a_3$ illustrated in FIG. 2B all denote the thickness of the plaque portion. That is, in FIG. 2B, the cross x represents the pixel included in the surface of the plaque portion, and the filled circle represents the pixel included in the surface of the second plaque portion along the straight line. The plaque/lime thickness measurement unit 142 measures the thickness of the plaque portion at the preset viewpoint position by counting up the number of pixels present between the crosses x and the filled circles. In addition, although not shown in the drawings, for example, the plaque/lime thickness measurement unit 142 similarly measures the thickness of the calcification portion. An initial value (for example, a radius from the start point or the like) may be previously set regarding how long each straight line drawn from the viewpoint position to the plaque portion extends to perform search, or the like.

Although the first embodiment is described by exemplifying a case where the plaque/lime thickness measurement unit 142 uses both plaque and calcification portions as the separation/extraction target, the embodiment is not limited thereby. For example, the embodiment may be similarly applied to a case where the plaque/lime thickness measurement unit 142 uses only either the plaque portion or the calcification portion as the separation/extraction target.

The color setting unit 143 performs color settings for a plaque portion and a calcification portion based on information on the measured spatial distribution. Specifically, first, the color setting unit 143 receives the voxel number as information on the measured thickness from the plaque/lime thickness measurement unit 142. Next, the color setting unit 143 obtains the color setting corresponding to the voxel number received from the plaque/lime thickness measurement unit 142 with reference to a matching table between the voxel number and the color settings. In addition, the color setting unit 143 sends the obtained color settings to the display control unit 144.

FIG. 3 is a diagram illustrating a matching table between the voxel number and the color settings. As shown in FIG. 3, in the first embodiment, the color setting unit 143 assigns a blue color to a plaque portion and a calcification portion and increases the density thereof depending on the voxel number. In addition, the color setting unit 143 receives the voxel number from the plaque/lime thickness measurement unit 142 as many as the number of straight lines searched in a radial fashion with respect to the entire plaque portion by using the viewpoint position as a start point. Accordingly, the color setting unit 143 obtains color settings corresponding to each received voxel number. In addition, if the voxel number has a value "0," it means the corresponding straight line does not pass through the plaque portion. Therefore, the color setting unit 143 may not perform color setting.

The display control unit 144 performs control such that the fly-through images and information on spatial distribution are displayed. Specifically, first, the display control unit 144 receives the color settings for each the straight line searched in a radial fashion with respect to the entire plaque portion by using the viewpoint position as a start position (excluding a straight line that does not pass through the plaque portion). Next, the display control unit 144 displays the fly-through image sent from the fly-through image creation unit 141 in the display unit 112. Here, the display control unit 144 displays the plaque portion based on the color settings received from the color setting unit 143.

FIGS. 4A to 4F and 5A to 5F are diagrams illustrating coloring of a plaque portion. FIGS. 4A to 4F and 5A to 5F all illustrate a plaque portion formed in a vascular wall. The plaque portion illustrated in FIG. 4A has a relatively thick width (depth) along a traveling direction in the vessel compared to the plaque portion illustrated in FIG. 4B.

Figure 4A:
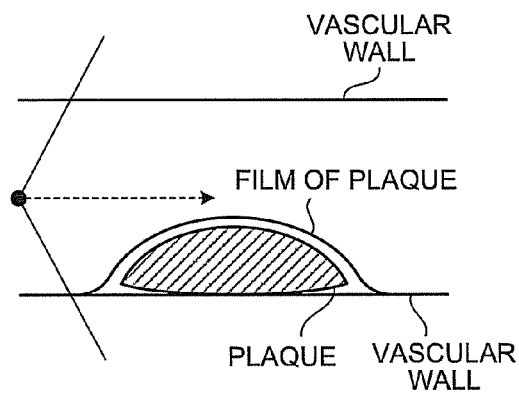
FIGS. 4A to 4F are diagrams illustrating coloring of a plaque portion.
Figure 4B:
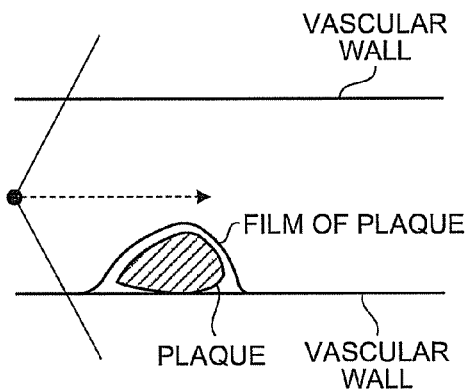
Figure 4C:
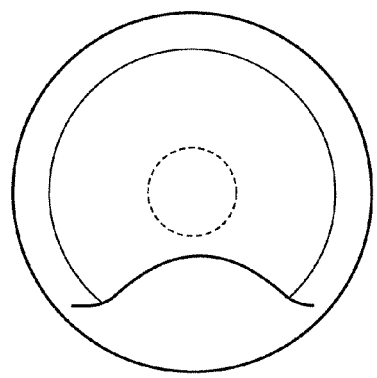
Figure 4D:
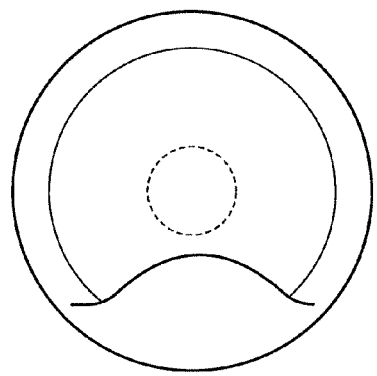

FIGS. 4C and 4D illustrate a fly-through image before the color setting. The outermost circle represents the outer edge of the fly-through image. In addition, the innermost circle (circled by a dotted line) represents a fact that the fly-through image has a depth (the fly-through image is taken by observing the internal side of the vessel).

That is, FIG. 4C corresponds to a fly-through image of the vessel of FIG. 4A observed from the viewpoint position, and FIG. 4D corresponds to a fly-through image of the vessel of FIG. 4B observed from the viewpoint position. As such, since the fly-through image before the color setting merely displays superficial information, it is failed to display information on the spatial distribution such as the thickness of the plaque portion.

Figure 4E:
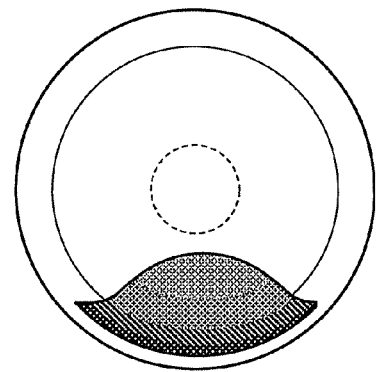
Figure 4F:
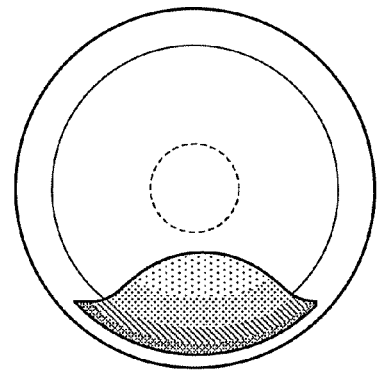

Both FIGS. 4E and 4F illustrate the fly-through image after the color setting, which also show the fly-through images displayed in the display unit 112 using the display control unit 144 according to the first embodiment. FIG. 4E corresponds to the fly-through image of the vessel of FIG. 4A observed from the viewpoint position, and FIG. 4F corresponds to the fly-through image of the vessel of FIG. 4B observed from the viewpoint position. In addition, in FIGS. 4E and 4F, for the purpose of simplicity in description, a blue color is represented in gray or black. For example, a blue color having a deep density is represented in black, and a blue color having a shallow density is represented in gray.

That is, the display control unit 144 displays the surface of the plaque portion present along the straight line searched in a radial fashion as a fly-through image using the density of the color setting received from the color setting unit 143. Then, the thickness in a depthwise direction in a case where the plaque portion is observed from the viewpoint position is expressed using the density. For example, comparing FIGS. 4E with 4F, the superficial shapes of the plaque portions are the same, but the blue color of FIG. 4E is expressed deeper than that of FIG. 4F in density. For this reason, an operator recognizes that the plaque portion illustrated in FIG. 4E has a thicker width (or depth) in a traveling direction of the vessel.

Figure 5A:
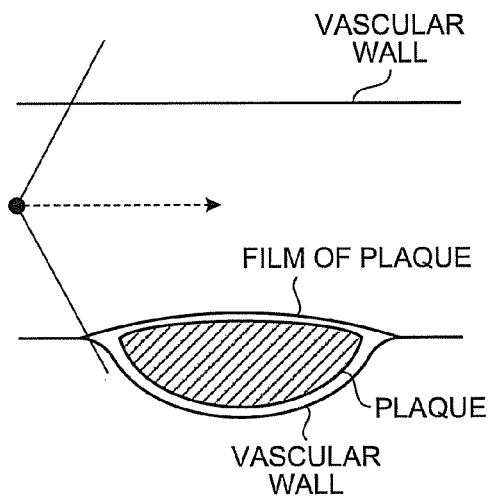
FIGS. 5A to 5F are diagrams illustrating coloring of a plaque portion.
Figure 5B:
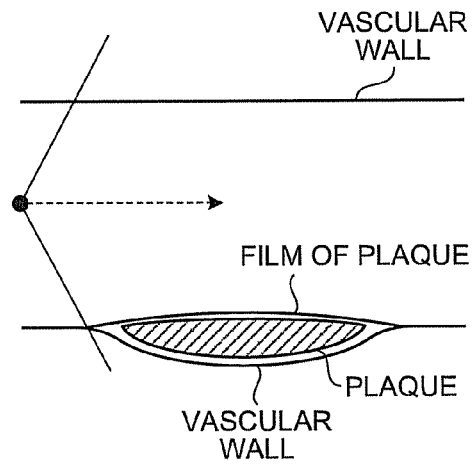

Similarly, both FIGS. 5A and 5B illustrate a plaque portion formed in a vascular wall. First of all, although the plaque portions illustrated in FIGS. 4A and 4B adhere to an internal site of the vessel as if they bulge inside the vessel, the plaque portions illustrated in FIGS. 5A and 5B adhere to an internal site of the vessel and have a relatively flat surface. In addition, it is recognized that the plaque portion illustrated in FIG. 5A has a larger thickness from the vascular wall than the plaque portion illustrated in FIG. 5B.

Figure 5C:
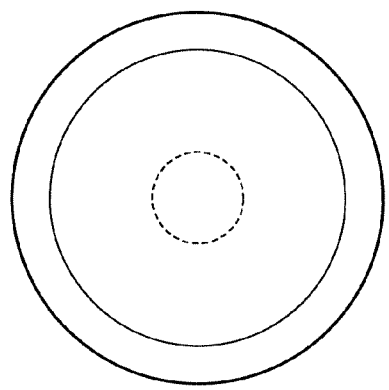
Figure 5D:
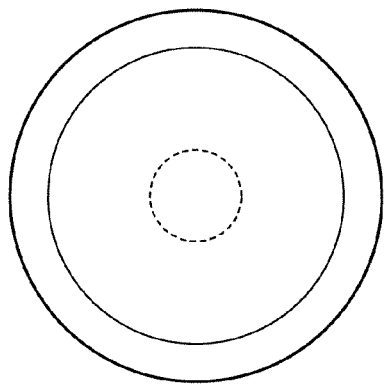

Both FIGS. 5C and 5D illustrate the fly-through images before the color setting. FIG. 5C corresponds to a fly-through image of the vessel of FIG. 5A observed from the viewpoint position, and FIG. 5D corresponds to a fly-through image of the vessel of FIG. 5B observed from the viewpoint position. First of all, in FIGS. 5A to 5F, the plaque portions adhere to the internal site of the vessel and have a relatively flat surface. Therefore, the fly-through image before the color setting fails to display information on the spatial distribution of the plaque portion and still fails to display the plaque portion itself.

Figure 5E:
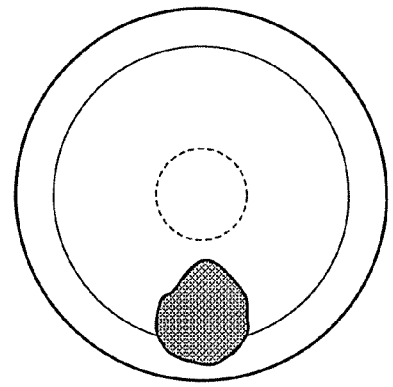
Figure 5F:
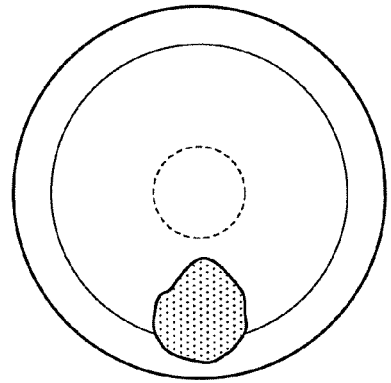

Both FIGS. 5E and 5F illustrate the fly-through images before the color setting, which are displayed in the display unit 112 using the display control unit 144 according to a first embodiment. FIG. 5E corresponds to a fly-through image of the vessel of FIG. 5A observed from the viewpoint position, and FIG. 5F corresponds to a fly-through image of the vessel of FIG. 4B observed from the viewpoint position.

For example, comparing FIGS. 5E and 5F, the superficial shapes of the plaque portions are the same, but FIG. 5E is expressed in blue which means a high density as compared with FIG. 5F. For this reason, an operator can see that the plaque portion illustrated in FIG. 5E has a large thickness from the vascular wall.

Figure 6A:
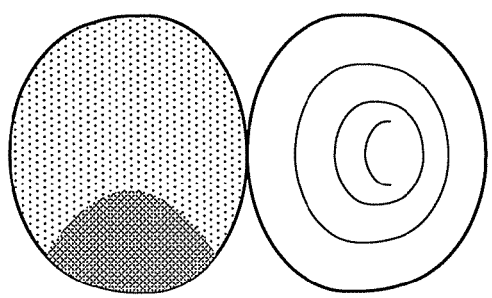
FIGS. 6A and 6B are diagrams illustrating coloring of a plaque portion.
Figure 6B:
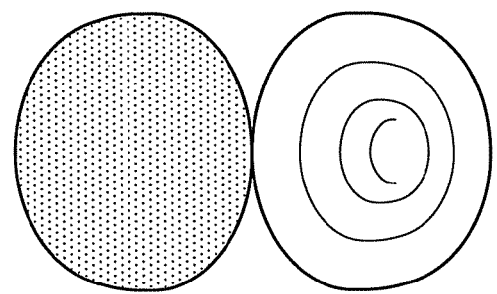

In addition, FIGS. 6A and 6B illustrate the fly-through images obtained by observing a split point of the vessel, in which the left vessel is perfectly occluded by the plaque. Both FIGS. 6A and 6B illustrate the fly-through images on which the color setting has been performed, and also the fly-through images displayed on the display unit 112 under the control of the display control unit 144 according to the first embodiment.

For example, comparing FIGS. 6A with 6B, although the left vessel is colored in blue in both figures, the left vessel of the FIG. 6A is expressed deeper than FIG. 6B in density. For this reason, an operator can see that the occlusion of FIG. 6A is thicker in a depthwise direction, and the lower portion of the vessel is relatively thick.

Figure 7:
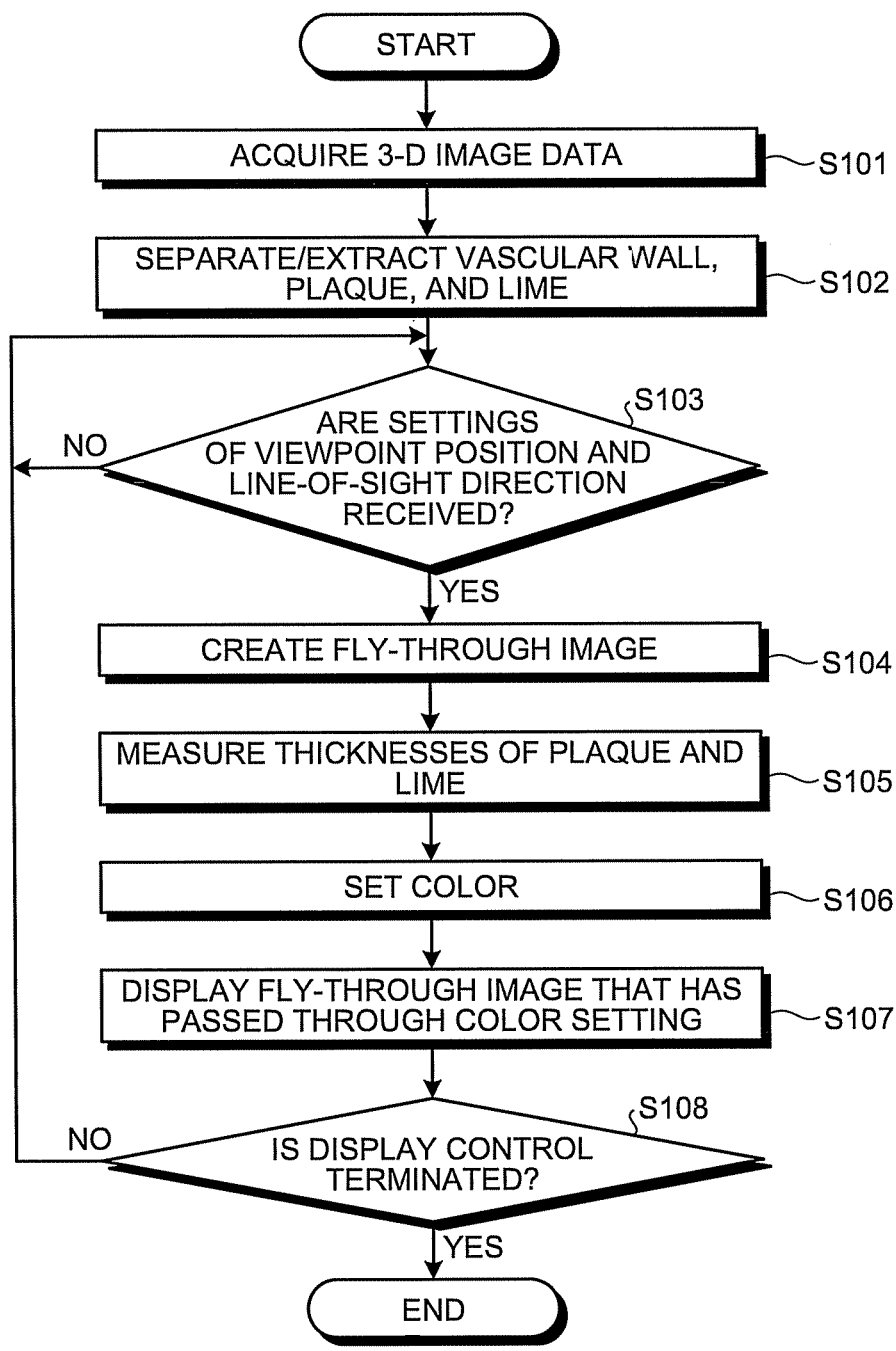
FIG. 7 is a flowchart illustrating the sequence of processing using the image processing apparatus according to the first embodiment.

Next, the sequence of processing in the image processing apparatus 100 according to the first embodiment will be described. FIG. 7 is a flowchart illustrating the sequence of processing using the image processing apparatus 100 according to the first embodiment.

First, the plaque/lime separation/extraction unit 130 obtains 3-dimensional image data from the 3-dimensional image data storage unit 120 in Step S101, analyzes the obtained 3-dimensional image data, and separates/extracts the vascular wall, the plaque portion, and the calcification portion in Step S102.

In addition, the fly-through image creation unit 141 determines whether the settings for the viewpoint position and the line-of-sight direction are received in step S103. If it is determined that the settings are received (YES in Step S103), the fly-through image creation unit 141 creates a fly-through image in Step S104.

Next, the plaque/lime thickness measurement unit 142 measures the thicknesses of a plaque portion and a calcification portion based on a preset viewpoint position in step S105, and the color setting unit 143 performs color settings for the plaque portion and the calcification portion in step S106.

Subsequently, the display control unit 144 performs control such that the fly-through image subjected to the color setting is displayed in the display unit 112 in Step S107. Then, the image processing apparatus 100 determines whether or not termination of display control for the fly-through image is received in Step S108. When it is received (YES in Step S108), the process ends.

Meanwhile, when it is not received (NO in Step S108), the image processing apparatus 100 returns the processing to a process of determining whether or not the fly-through image creation unit 141 has received settings for parameters including the viewpoint position, the line-of-sight direction, and the field-of-view angle.

In addition, FIG. 7 illustrates merely an example of the processing sequence in the image processing apparatus 100 according to the first embodiment, and is not intended to limit the embodiment. For example, it is acceptable that the process of Step S102 continues up to Step S105. Further, it may be performed in parallel with the process of Step S104.

As described above, in the first embodiment, the fly-through image creation unit 141 creates the fly-through image observed from the preset viewpoint position along the preset line-of-sight direction based on the 3-dimensional image data collected by the medical image diagnosis apparatus 1. In addition, the plaque/lime separation/extraction unit 130 analyzes the 3-dimensional image data to designate the plaque portion and the calcification portion. Next, the plaque/lime thickness measurement unit 142 measures information on the spatial distribution of the plaque portion and the calcification portion designated by the plaque/lime separation/extraction unit 130. In addition, the color setting unit 143 and the display control unit 144 perform control such that the fly-through image created by the fly-through image creation unit 141 and the information on the spatial distribution measured by the plaque/lime thickness measurement unit 142 are displayed.

In this manner, according to the first embodiment, it is possible to display information on the spatial distribution of the plaque portion or the calcification portion on the fly-through image. In addition, since the information on the spatial distribution that has not been originally observed is displayed on the fly-through image, an operator can recognize the information on the spatial distribution of the plaque portion or the calcification portion. Furthermore, according to the first embodiment, it is possible to support an ischemic heart disease diagnosis or a curative program review.

Next, an image processing apparatus 100 according to a second embodiment will be described. The image processing apparatus 100 according to the second embodiment creates a vessel image representing a traveling direction of a vessel in addition to a fly-through image from 3-dimensional image data and displays the created vessel image. In addition, the image processing apparatus 100 according to the second embodiment receives settings for a viewpoint position and a line-of-sight direction on the displayed vessel image and creates a fly-through image observed using the received viewpoint position and the received line-of-sight direction. That is, the image processing apparatus 100 according to the second embodiment receives the settings for viewpoint position and the line-of-sight direction of the fly-through image on the vessel image.

Figure 8:
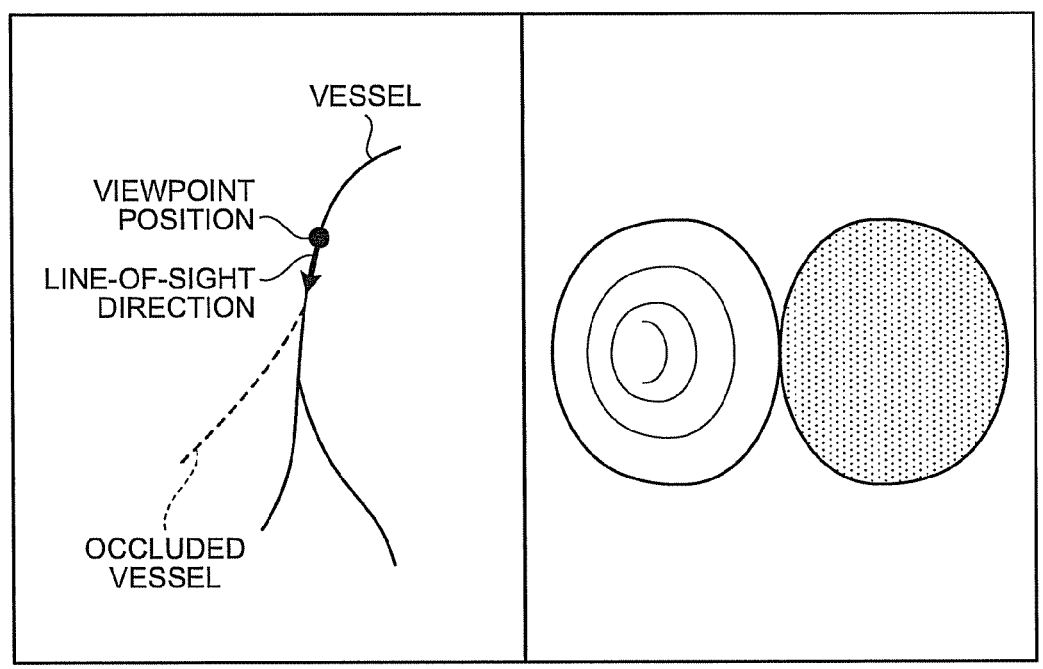
FIG. 8 is a diagram illustrating an overview of an image processing apparatus according to a second embodiment.

FIG. 8 is a diagram illustrating an overview of the image processing apparatus 100 according to the second embodiment. As shown in FIG. 8, for example, the image processing apparatus 100 according to the second embodiment displays a vessel image on the left half of a display unit 112 and displays a fly-through image on the right half of thereof. For example, the vessel image of FIG. 8 shows vessel traveling information, the viewpoint position, and the line-of-sight direction. In FIG. 8, the occluded vessel is displayed as a dotted line.

The image processing apparatus 100 according to the second embodiment receives the settings for the viewpoint position and the line-of-sight direction on the displayed vessel image. For example, the image processing apparatus 100 receives the settings for the viewpoint position and the line-of-sight direction when a user changes the position of the black arrow or the direction of the arrow by clicking and dragging the black arrow shown in FIG. 8 using a mouse.

The image processing apparatus 100 according to the second embodiment creates the fly-through image observed using the received viewpoint position and the received line-of-sight direction, and displays the fly-through image, for example, as shown in FIG. 8. That is, when a user clicks and drags the black arrow illustrated in FIG. 8 using a mouse, the fly-through image of the right half changes in synchronization with user's operation. The embodiment may not be limited to a multi-screen display method but be also similarly applied to a method of displaying the vessel image and the fly-through image in a manner of switching screens.

Figure 9:
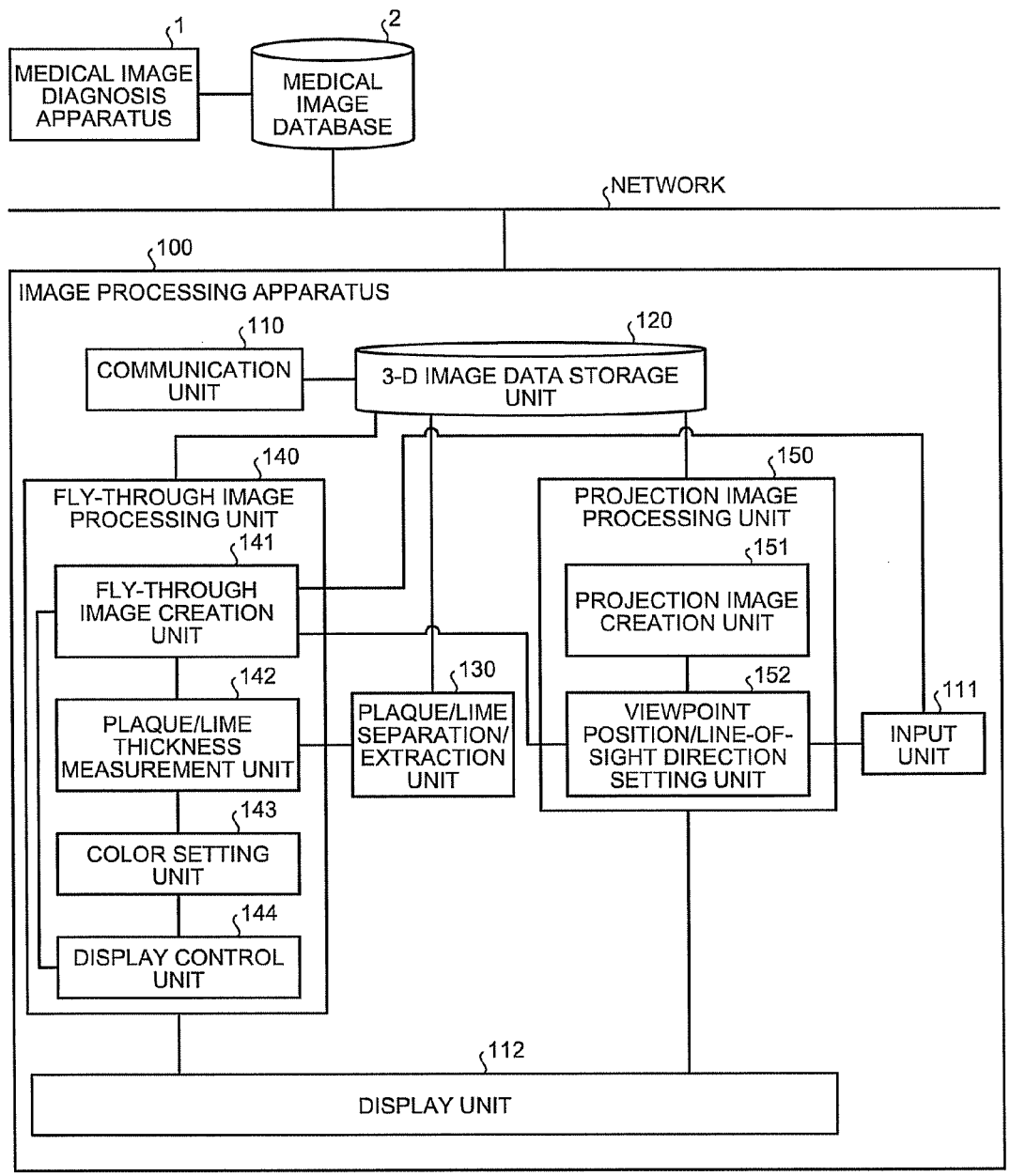
FIG. 9 is a block diagram illustrating the configuration of the image processing apparatus according to the second embodiment.

FIG. 9 is a block diagram illustrating the configuration of the image processing apparatus 100 according to the second embodiment. As shown in FIG. 9, the image processing apparatus 100 according to the second embodiment further includes a projection image processing unit 150. The projection image processing unit 150 includes a projection image creation unit 151 and a viewpoint position/line-of-sight direction setting unit 152.

The projection image creation unit 151 creates a vessel image representing the traveling direction of the vessel based on the 3-dimensional image data and displays the created vessel image. Specifically, first, the projection image creation unit 151 creates the vessel image representing a traveling direction of the vessel based on the 3-dimensional image data read from the 3-dimensional image data storage unit 120. Then, the projection image creation unit 151 displays the created vessel image in the display unit 112. In addition, the projection image creation unit 151 displays the black arrow for receiving settings for the viewpoint position and the line-of-sight direction from a user, for example, at an initial setting position or the like.

The viewpoint position/line-of-sight direction setting unit 152 receives settings for the viewpoint position and the line-of-sight direction on the vessel image. Specifically, the viewpoint position/line-of-sight direction setting unit 152 receives settings for the projection image creation unit 151 by receiving manipulation from a user through the input unit 111 on the vessel image displayed in the display unit 112 using the projection image creation unit 151. In addition, the viewpoint position/line-of-sight direction setting unit 152 sends the received settings for the viewpoint position and the line-of-sight direction to the fly-through image creation unit 141 of the fly-through image processing unit 140.

Then, the fly-through image creation unit 141 according to the second embodiment creates the fly-through image observed using the viewpoint position and the line-of-sight direction received from the viewpoint position/line-of-sight direction setting unit 152, notifies the plaque/lime thickness measurement unit 142 of the viewpoint position and the line-of-sight direction, and sends the created fly-through image to the display control unit 144.

Subsequently, the plaque/lime thickness measurement unit 142 according to the second embodiment measures again the thicknesses of the plaque portion and the calcification portion with respect to the viewpoint position, that is newly set, and the color setting unit 143 performs again the color setting for the plaque portion and the calcification portion based on information on the measured thicknesses. Then, the display control unit 144 performs control again such that the thickness is displayed together with the fly-through image.

Figure 10:
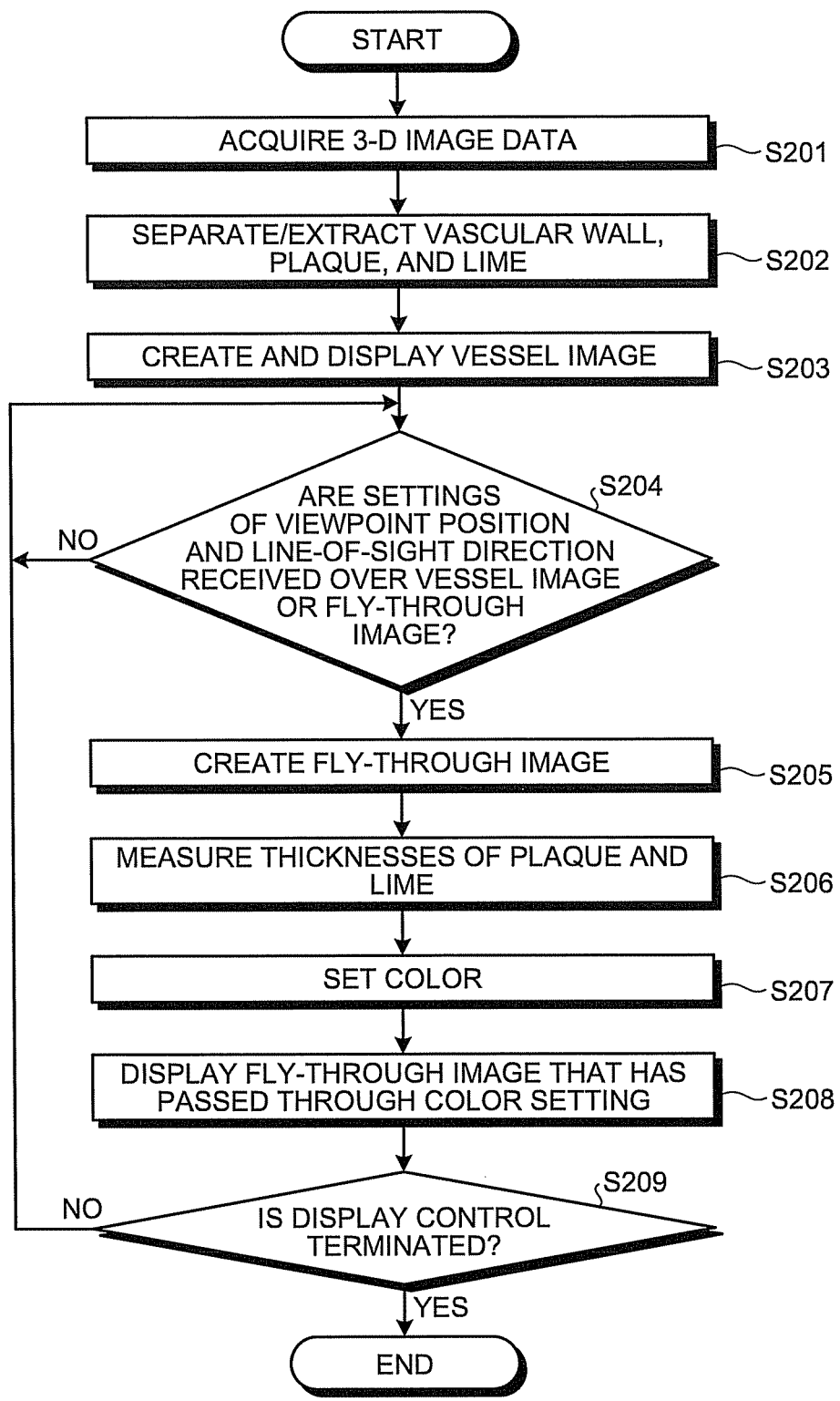
FIG. 10 is a flowchart illustrating the sequence of processing using the image processing apparatus according to the second embodiment.

Next, a processing sequence of the image processing apparatus 100 according to the second embodiment will be described. FIG. 10 is a flowchart illustrating a processing sequence using the image processing apparatus 100 according to the second embodiment.

First, in the second embodiment, the plaque/lime separation/extraction unit 130 and the projection image creation unit 151 acquire the 3-dimensional image data from the 3-dimensional image data storage unit 120 in Step S201. In addition, the plaque/lime separation/extraction unit 130 analyzes the obtained 3-dimensional image data to separate/extract a vascular wall, a plaque portion, and a calcification portion as in the first embodiment in Step S202. Meanwhile, the projection image creation unit 151 creates a vessel image based on the obtained 3-dimensional image data and displays the vessel image in the display unit 112 in Step S203.

Subsequently, in the second embodiment, the fly-through image creation unit 141 determines whether or not the settings for the viewpoint and the line-of-sight direction are received over the fly-through image, the viewpoint position/line-of-sight direction setting unit 152 also determines whether or not the settings for the viewpoint position and the line-of-sight direction are received over the vessel image in Step S204.

In addition, if it is determined that the fly-through image creation unit 141 or the viewpoint position/line-of-sight direction setting unit 152 received the settings for the viewpoint and the line-of-sight direction, the fly-through image creation unit 141 creates the fly-through image in Step S205.

Then, the plaque/lime thickness measurement unit 142 measures the thicknesses of the plaque portion and the calcification portion based on a preset viewpoint position in Step S206, and the color setting unit 143 performs the color setting for the plaque portion and the calcification portion based on information on the measured thicknesses in Step S207.

Subsequently, the display control unit 144 performs control such that the fly-through image subjected to the color setting is displayed on the display unit 112 in Step S208. Then, the image processing apparatus 100 determines whether or not termination of the display control for the fly-through image is received in Step S209. When termination is received (YES in Step S209), the process ends.

Meanwhile, when the termination is not received (NO in Step S209), the image processing apparatus 100 returns the processing to the process of determining whether or not the fly-through image creation unit 141 and the viewpoint position/line-of-sight direction setting unit 152 receive the settings for the viewpoint position and the line-of-sight direction.

FIG. 10 illustrates an example of the processing sequence using the image processing apparatus 100 according to the second embodiment, and the embodiment is not limited thereby. For example, it is acceptable that the process of Step S203 continues up to Step S204. It may be also performed in parallel with Step S202.

As described above, according to the second embodiment, the projection image creation unit 151 creates the vessel image representing the traveling direction of the vessel based on the 3-dimensional image data and displays the created vessel image. In addition, the viewpoint position/line-of-sight direction setting unit 152 receives the settings for the viewpoint position and the line-of-sight direction over the vessel image displayed by the projection image creation unit 151. The fly-through image creation unit 141 creates the fly-through image observed using the viewpoint position and the line-of-sight direction received by the viewpoint position/line-of-sight direction setting unit 152. In this manner, according to the second embodiment, an operator can readily recognize the internal side of the vessel regarding which position and which direction are used in the observation.

Subsequently, an image processing apparatus 100 according to a third embodiment will be described. The image processing apparatus 100 according to the third embodiment receives designation of a range for deleting a plaque portion and a calcification portion on a fly-through image. The image processing apparatus 100 according to the third embodiment creates a fly-through image based on 3-dimensional image data by deleting the plaque portion and the calcification portion corresponding to the received deletion range.

Figure 11:
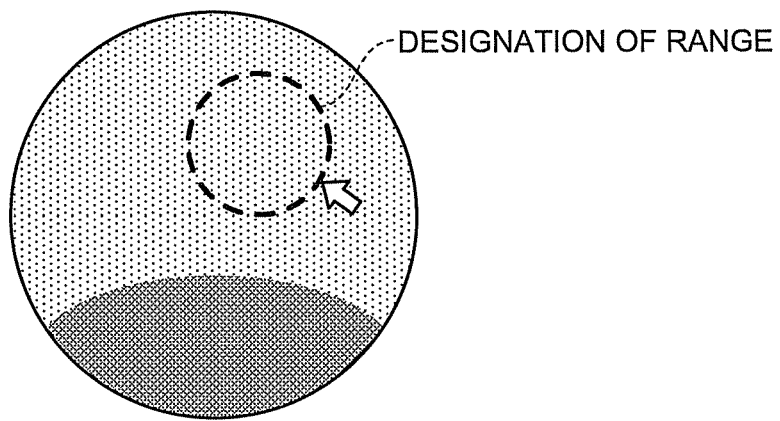
FIG. 11 is a diagram illustrating an overview of an image processing apparatus according to a third embodiment.
Figure 11:
Figure 11:
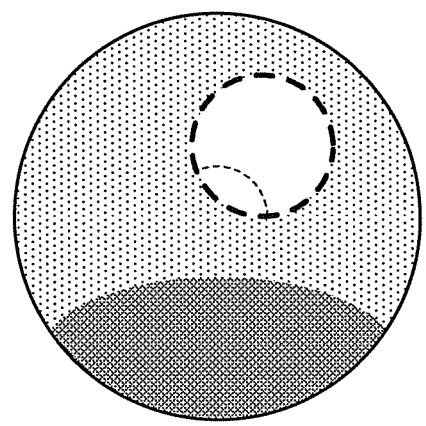

FIGS. 11(A) and 11(B) are diagrams illustrating an overview of the image processing apparatus 100 according to the third embodiment. FIG. 11(A) illustrates the fly-through image before receiving designation of the deletion range. As shown in FIG. 11(A), the image processing apparatus 100 according to the third embodiment receives designation of the deletion range over the displayed fly-through image. For example, when a user designates a range shown as a dotted line by clicking and dragging to draw a circle over the screen shown in FIG. 11(A) using a mouse, the image processing apparatus 100 receives designation of the deletion range. In addition, for the depthwise direction of the deletion range, an initial value or may be used, or a value may be set by an operator.

FIG. 11(B) illustrates the fly-through image in which the plaque portion and the calcification portion corresponding to the received deletion range are deleted. As shown in FIG. 11(B), the image processing apparatus 100 according to the third embodiment creates and displays the fly-through image by deleting the plaque portion and the calcification portion corresponding to the received deletion range based on 3-dimensional image data.

Figure 12:
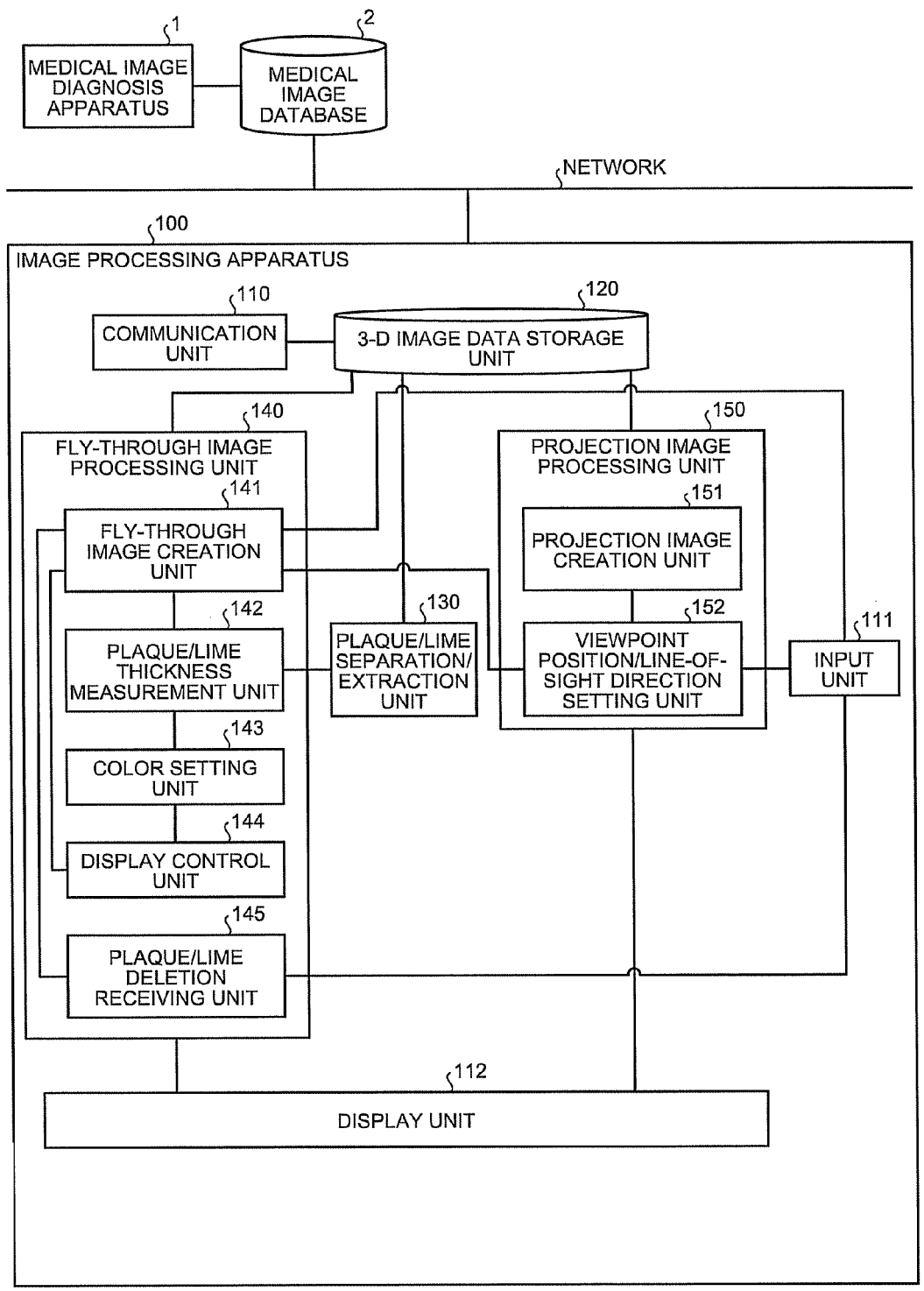
FIG. 12 is a block diagram illustrating the configuration of the image processing apparatus according to the third embodiment.

FIG. 12 is a block diagram illustrating the configuration of the image processing apparatus 100 according to the third embodiment. As shown in FIG. 12, the fly-through image processing unit 140 of the image processing apparatus 100 according to the third embodiment further includes a plaque/lime deletion receiving unit 145.

The plaque/lime deletion receiving unit 145 receives designation of the range for deleting the plaque portion and the calcification portion over the fly-through image. Specifically, the plaque/lime deletion receiving unit 145 receives designation of the deletion range by receiving manipulation from an operator using the input unit 111 over the fly-through image displayed in the display unit 112 under control of the display control unit 144. In addition, the plaque/lime deletion receiving unit 145 sends the received designation of the deletion range to the fly-through image creation unit 141. In addition, the plaque/lime deletion receiving unit 145 may receive, for example, the "entire area" as the designation of the deletion range.

Then, the fly-through image creation unit 141 according to the third embodiment creates the fly-through image observed when the deletion range received by the plaque/lime deletion receiving unit 145 is deleted. For example, the fly-through image creation unit 141 deletes pixels corresponding to the deletion range from the 3-dimensional image data and creates the fly-through image based on the 3-dimensional image data obtained after the deletion. In addition, the fly-through image creation unit 141 notifies the plaque/lime thickness measurement unit 142 of the deletion range and sends the created fly-through image to the display control unit 144.

Subsequently, the plaque/lime thickness measurement unit 142 according to the third embodiment measures again the thicknesses of the plaque portion and the calcification portion based on the information on the deletion range notified from the fly-through image creation unit 141, and the color setting unit 143 performs again the color setting for the plaque portion and the calcification portion based on information on the measured thicknesses. Then, the display control unit 144 performs control again such that the thicknesses are displayed together with the fly-through image.

Although description of the third embodiment has been made for an example in which the image processing apparatus 100 according to the third embodiment includes the projection image processing unit 150 similar to the second embodiment and creates the fly-through image observed using the viewpoint position and the line-of-sight direction received over the vessel image as in the second embodiment, the embodiment is not limited thereby. For example, the image processing apparatus 100 according to the third embodiment may be configured by excluding the projection image processing unit 150 as in the first embodiment.

Figure 13:
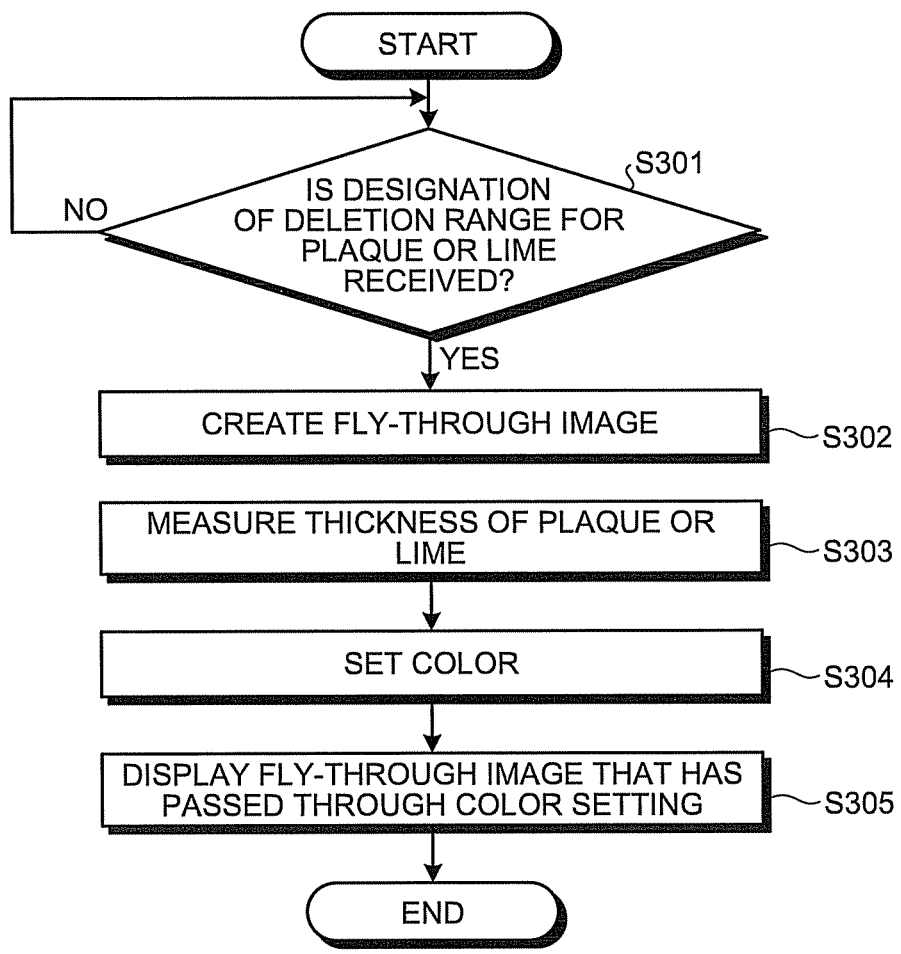
FIG. 13 is a flowchart illustrating the sequence of processing using an image processing apparatus according to the third embodiment.

Next, a processing sequence using the image processing apparatus 100 according to the third embodiment will be described. FIG. 13 is a flowchart illustrating a processing sequence using the image processing apparatus 100 according to the third embodiment. That is, the image processing apparatus 100 according to the third embodiment further performs a process of receiving the designation of the deletion range by the plaque/lime deletion receiving unit 145 in addition to the processing sequence illustrated in FIG. 7 similar to the first embodiment so that the processing sequence shown in FIG. 13 is performed when the designation of the deletion range is received. Hereinafter, the processing sequence illustrated in FIG. 13 will be described.

In the third embodiment, it is determined whether or not the plaque/lime deletion receiving unit 145 receives the designation of the deletion range for the plaque portion and the calcification portion in Step S301. When the plaque/lime deletion receiving unit 145 has not received the designation of the deletion range (NO in Step S301), the plaque/lime deletion receiving unit 145 returns to the processing to the process of determining whether or not the designation of the deletion range for the plaque portion and the calcification portion is received.

Meanwhile when plaque/lime deletion receiving unit 145 has received the designation of the deletion range (YES in Step S301), the fly-through image creation unit 141 creates the fly-through image observed when the received deletion range is deleted in Step S302.

Then, the plaque/lime thickness measurement unit 142 measures the thickness of the plaque portion and the calcification portion for a case where the deletion range is deleted in Step S303 and performs the color setting for the plaque portion and the calcification portion based on information on the measured thicknesses in Step S304. Subsequently, the display control unit 144 performs control such that the fly-through image subjected to the color setting is displayed on the display unit 112 in Step S305.

As described above, in the third embodiment, the plaque/lime deletion receiving unit 145 receives the designation of the range for deleting the plaque portion and the calcification portion over the fly-through image displayed under control of the display control unit 144. In addition, the fly-through image creation unit 141 creates the fly-through image obtained by deleting the plaque portion and the calcification portion corresponding to the range received by the plaque/lime deletion receiving unit 145 based on the 3-dimensional image data. In addition, the plaque/lime thickness measurement unit 142 measures information on the spatial distribution of the plaque portion and the calcification portion for a case where the range received by the plaque/lime deletion receiving unit 145 is deleted. Furthermore, the color setting unit 143 and the display control unit 144 perform control to display the fly-through image created by the fly-through image creation unit 141 and information on the spatial distribution measured by the plaque/lime thickness measurement unit 142. Through the aforementioned process, an operator is allowed to virtually experience the deletion process for the plaque portion or the calcification portion over the fly-through image, for example, before treatment.

The embodiment may be embodied in other forms in addition to the foregoing embodiments.

In the foregoing description of the embodiments, as a method of measuring the thickness of the plaque portion or the calcification portion, a method of counting up the number of pixels present along a straight line drawn from the viewpoint position to the plaque portion or the like has been exemplified. However, the embodiment of the embodiment is not limited thereby.

For example, the plaque/lime thickness measurement unit 142 may measure the thickness of the plaque portion or the calcification portion based on a relationship with a core line. FIGS. 14A, 14B, 15A, and 15B are diagrams illustrating thickness measurement for the plaque portion and the calcification portion according to another embodiment of the embodiment.

Figure 14A:
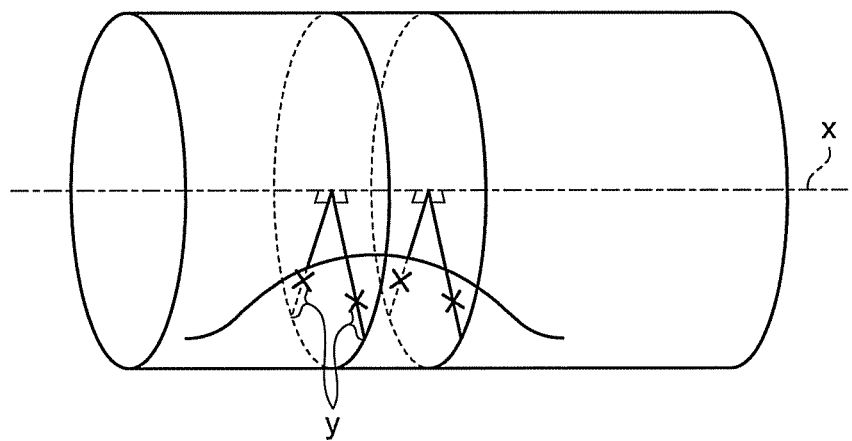
FIGS. 14A and 14B are diagrams illustrating measurement of thicknesses of a plaque portion and a calcification portion according to another embodiment.
Figure 14B:
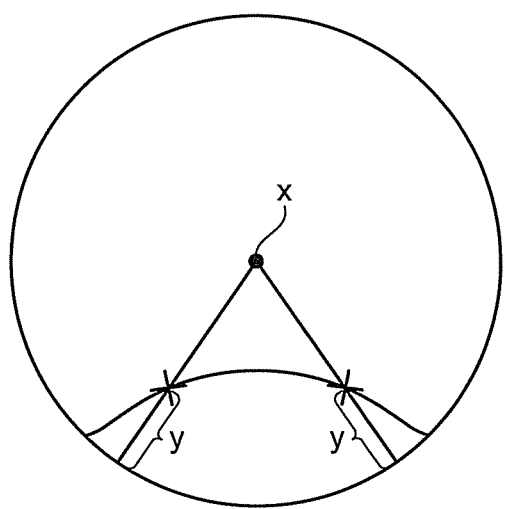

First, as shown in FIGS. 14A and 14B, for example, it is assumed that a plaque portion adheres to an internal site of the vessel as if it bulges inside the vessel. In addition, FIG. 14B is a diagram illustrating the vessel of FIG. 14A observed from the left direction. In this case, the plaque/lime thickness measurement unit 142 draws a perpendicular line from the core line x of the vessel to the vascular wall. As shown in FIG. 14A, a plurality of perpendicular lines are drawn to search for the surfaces perpendicular to the core line x. In addition, the plaque/lime thickness measurement unit 142 counts up the number of pixels (voxel number) having a CT value representing the "plaque" along each the perpendicular line. For example, all of the reference symbols y illustrated in FIGS. 14A and 14B denote the thickness of the plaque portion. In addition, in FIGS. 14A and 14B, the reference symbols x denote pixels included in the surface (inner surface) of the plaque portion. The plaque/lime thickness measurement unit 142 measures the thickness of the plaque portion by counting up the number of pixels having a CT value representing the "plaque" along each perpendicular line. Although not shown in the drawings, for example, the plaque/lime thickness measurement unit 142 measures the thickness of the calcification portion similarly.

Figure 15A:
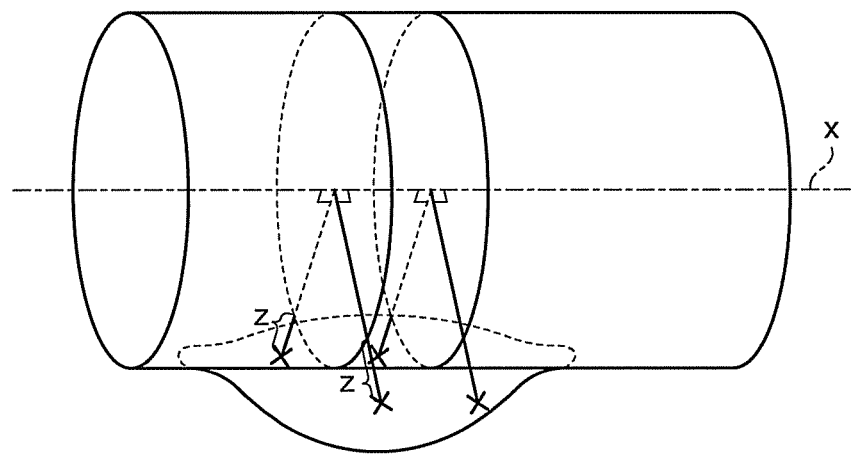
FIGS. 15A and 15B are diagrams illustrating measurement of thicknesses of a plaque portion and a calcification portion according to still another embodiment.
Figure 15B:
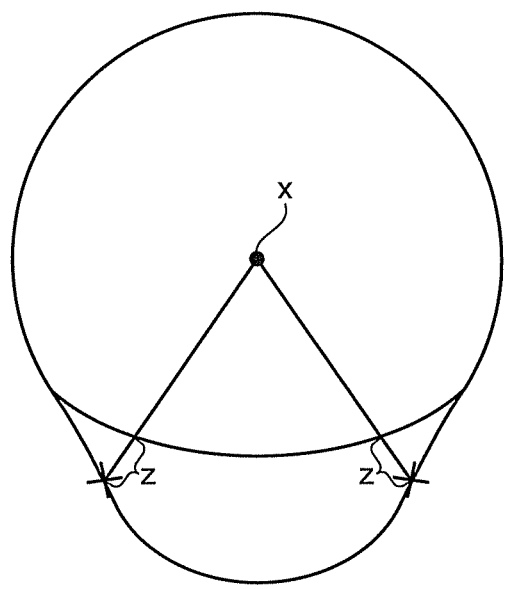

Similarly, although FIGS. 15A and 15B illustrate the plaque portion formed in the vascular wall, for example, the plaque portion adheres to an internal site of the vessel while the surface thereof is formed to be relatively flat. FIG. 15B is a diagram illustrating the vessel of FIG. 15A observed from the left direction. In this case, the plaque/lime thickness measurement unit 142 draws a perpendicular line from the core line x of the vessel to the vascular wall. As shown in FIG. 15A, a plurality of perpendicular lines are drawn to search for the surface perpendicular to the core line x. In addition, the plaque/lime thickness measurement unit 142 counts up the number of pixels (voxel number) having a CT value representing the "plaque" along each perpendicular line. For example, all of the reference symbols z illustrated in FIGS. 15A and 15B denote the thickness of the plaque portion. That is, the reference symbols x illustrated in FIGS. 15A and 15B denote the pixel included in the surface (outer surface) of the plaque portion. The plaque/lime thickness measurement unit 142 measures the thickness of the plaque portion by counting up the number of pixels having a CT value representing the "plaque" along each perpendicular line. In addition, although not shown in the drawings, the plaque/lime thickness measurement unit 142 also measures the thickness for the calcification portion similarly.

When the thickness of the plaque portion or the calcification portion is measured through the aforementioned method, the thickness of the plaque portion or the calcification portion remains constant without being affected by the viewpoint position. That is, the display control unit 144 displays the fly-through image with respect to the viewpoint position and displays the plaque portion based on the certain color setting received from the color setting unit 143.

Although the foregoing embodiments have been described for a method in which the plaque/lime thickness measurement unit 142 measures the thickness of the plaque portion by counting up the voxel number, and the color setting unit 143 performs color setting corresponding to the counted voxel number, the embodiment is not limited thereby. For example, the plaque/lime thickness measurement unit 142 may compute an integration value of the CT values without counting up the voxel number, and the color setting unit 143 may perform the color setting corresponding to the computed integration value.

In addition, for example, the plaque/lime thickness measurement unit 142 may obtain a maximum value (a minimum value, an average value, or the like) without counting up the voxel number, and the color setting unit 143 may perform color setting corresponding to the obtained maximum value ((a minimum value, an average value, or the like). That is, for example, in the case of the calcification portion, it is envisaged that the CT values vary as the stiffness of the portion varies depending on the progress status of the calcification. If so, the image processing apparatus 100 may obtain meaningful values such as the maximum or minimum value of the CT values in a medical sense, and the color setting may be performed based on such values. As a result, it is possible to display the progress status of the calcification portion by placing more emphasis.

Although the foregoing embodiments have been described for a method in which the information on the spatial distribution is expressed using densities of the colors set for the plaque portion and the calcification portion, the embodiment is not limited thereby. For example, the spatial distribution may be expressed using a change in brightness. In addition, for example, different colors may be used for each of the vascular wall, the plaque portion, or the calcification portion.

Although the foregoing embodiments have been described for an example in which the image processing apparatus 100 is contained in a casing different from the medical image diagnosis apparatus 1, the embodiment is not limited thereby. For example, the image processing apparatus 100 may be included in the medical image diagnosis apparatus 1.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing apparatus comprising:
    a creation unit configured to create a virtual endoscopic image observed using a preset viewpoint position and a preset line-of-sight direction based on 3-dimensional image data collected by a medical image diagnosis apparatus;
    a designation unit configured to analyze the 3-dimensional image data and designates a plaque portion and/or a calcification portion;
    a measurement unit configured to measure thickness of the plaque portion and/or the calcification portion designated by the designation unit; and
    a display control unit configured to perform control such that the virtual endoscopic image created by the creation unit and information on the thickness measured by the measurement unit are displayed,
    wherein the thickness is determined between two surfaces of the plaque portion and/or the calcification portion along the preset line-of-sight direction from the preset view point position.

2. The image processing apparatus according to claim 1, wherein the display control unit is configured to express the information on the thickness using a density or a brightness of a color which is set for the plaque portion and/or the calcification portion.

3. The image processing apparatus according to claim 1, further comprising:
    a vessel image display unit configured to create a vessel image representing a traveling direction of a vessel based on the 3-dimensional image data and displays the created vessel image; and
    a receiving unit configured to receive settings for a viewpoint position and a line-of-sight direction over the vessel image displayed by the vessel image display unit,
    wherein the creation unit is configured to create a virtual endoscopic image observed using the viewpoint position and the line-of-sight direction received by the receiving unit.

4. The image processing apparatus according to claim 2, further comprising:
    a vessel image display unit configured to create a vessel image representing a traveling direction of a vessel based on the 3-dimensional image data and displays the created vessel image; and
    a receiving unit configured to receive settings for a viewpoint position and a line-of-sight direction over the vessel image displayed by the vessel image display unit,
    wherein the creation unit is configured to create a virtual endoscopic image observed using the viewpoint position and the line-of-sight direction received by the receiving unit.

5. The image processing apparatus according to claim 1, further comprising:
    a deletion receiving unit configured to receive designation of a range for deleting the plaque portion and/or the calcification portion over the virtual endoscopic image displayed under control of the display control unit;
    a post-deletion creation unit configured to create a virtual endoscopic image based on the 3-dimensional image data by deleting the plaque portion and/or the calcification portion corresponding to the range received by the deletion receiving unit;
    a post-deletion measurement unit configured to measure the thickness of the plaque portion and/or the calcification portion designated by the designation unit for a case where the range received by the deletion receiving unit is deleted; and
    a post-deletion display control unit configured to perform control to display the virtual endoscopic image created by the post-deletion creation unit and the information on the thickness measured by the post-deletion measurement unit.

6. The image processing apparatus according to claim 2, further comprising:
    a deletion receiving unit configured to receive designation of a range for deleting the plaque portion and/or the calcification portion over the virtual endoscopic image displayed under control of the display control unit;
    a post-deletion creation unit configured to create a virtual endoscopic image based on the 3-dimensional image data by deleting the plaque portion and/or the calcification portion corresponding to the range received by the deletion receiving unit;
    a post-deletion measurement unit configured to measure the thickness of the plaque portion and/or the calcification portion designated by the designation unit for a case where the range received by the deletion receiving unit is deleted; and
    a post-deletion display control unit configured to perform control to display the virtual endoscopic image created by the post-deletion creation unit and the information on the thickness measured by the post-deletion measurement unit.

7. A medical image diagnosis apparatus comprising:
    a collecting unit configured to collect 3-dimensional image data obtained by capturing a vessel of a subject;
    a creation unit configured to create a virtual endoscopic image observed using a preset viewpoint position and a preset line-of-sight direction based on the 3-dimensional image data collected by the collecting unit;
    a designation unit configured to analyze the 3-dimensional image data and designates a plaque portion and/or a calcification portion;
    a measurement unit configured to measure thickness of the plaque portion and/or the calcification portion designated by the designation unit; and a display control unit configured to perform control to display the virtual endoscopic image created by the creation unit and information on the thickness measured by the measurement unit, wherein the thickness is determined between two surfaces of the plaque portion and/or the calcification portion along the preset line-of-sight direction from the preset view point position.

8. The medical image diagnosis apparatus according to claim 7, wherein the display control unit is configured to express the information on the thickness using a density or a brightness of a color which is set for the plaque portion and/or the calcification portion.

9. The medical image diagnosis apparatus according to claim 7, further comprising:

a vessel image display unit configured to create a vessel image representing a traveling direction of a vessel based on the 3-dimensional image data and displays the created vessel image; and a receiving unit configured to receive settings for a viewpoint position and a line-of-sight direction over the vessel image displayed by the vessel image display unit, wherein the creation unit is configured to create a virtual endoscopic image observed using the viewpoint position and the line-of-sight direction received by the receiving unit.

10. The medical image diagnosis apparatus according to claim 8, further comprising:

a vessel image display unit configured to create a vessel image representing a traveling direction of a vessel based on the 3-dimensional image data and displays the created vessel image; and a receiving unit configured to receive settings for the viewpoint position and the line-of-sight direction over the vessel image displayed by the vessel image display unit, wherein the creation unit is configured to create a virtual endoscopic image observed using the viewpoint position and the line-of-sight direction received by the receiving unit.

11. The medical image diagnosis apparatus according to claim 7, further comprising:

a deletion receiving unit configured to receive designation of a range for deleting the plaque portion and/or the calcification portion over the virtual endoscopic image displayed under control of the display control unit;

a post-deletion creation unit configured to create a virtual endoscopic image based on the 3-dimensional image data by deleting the plaque portion and/or the calcification portion corresponding to the range received by the deletion receiving unit;

a post-deletion measurement unit configured to measure the thickness of the plaque portion and/or the calcification portion designated by the designation unit for a case where the range received by the deletion receiving unit is deleted; and a post-deletion display control unit configured to perform control to display the virtual endoscopic image created by the post-deletion creation unit and the information on the thickness measured by the post-deletion measurement unit.

12. The medical image diagnosis apparatus according to claim 8, further comprising:

a deletion receiving unit configured to receive designation of a range for deleting the plaque portion and/or the calcification portion over the virtual endoscopic image displayed under control of the display control unit;

a post-deletion creation unit configured to create a virtual endoscopic image based on the 3-dimensional image data by deleting the plaque portion and/or the calcification portion corresponding to the range received by the deletion receiving unit;

a post-deletion measurement unit configured to measure the thickness of the plaque portion and/or the calcification portion designated by the designation unit for a case where the range received by the deletion receiving unit is deleted; and a post-deletion display control unit configured to perform control to display the virtual endoscopic image created by the post-deletion creation unit and the information on the thickness measured by the post-deletion measurement unit.

* * * * *